United States Patent [19]

Harris

[11] Patent Number: 5,077,443
[45] Date of Patent: Dec. 31, 1991

[54] PROCESS FOR THE LIQUID PHASE CHLORINATION OF 1,3-BUTADIENE

[75] Inventor: Alexander T. Harris, Metairie, La.

[73] Assignee: E. I. Du Pont de Nemours and Company, Wilmington, Del.

[21] Appl. No.: 631,266

[22] Filed: Dec. 20, 1990

Related U.S. Application Data

[63] Continuation-in-part of Ser. No. 438,549, Nov. 17, 1989, abandoned.

[51] Int. Cl.$^5$ ............................................. C07C 17/02
[52] U.S. Cl. .................................................. 570/231
[58] Field of Search ....................................... 570/231

[56] References Cited

U.S. PATENT DOCUMENTS 2,369,117  2/1945  Carter ................................. 570/231

FOREIGN PATENT DOCUMENTS 53-108908  9/1978  Japan .
53-137902  12/1978  Japan .
1435826  10/1973  United Kingdom .

Primary Examiner—Howard T. Mars

[57] ABSTRACT

Liquid phase chlorination in an evaporatively cooled reactor of 1,3-butadiene to 3,4-dichlorobutene-1 and 1,4-dichlorobutene-2 by contacting 1,3-butadiene and elemental chlorine in a solvent at a temperature of 25°–100° C. said solvent being butane or pentane or a fluorinated solvent of the formula $(CR_3)(CR'_2)_m(CR''_2)_nR$ where R is independently hydrogen, fluorine, chlorine or bromine, R' is hydrogen, R" is independently fluorine, chlorine or bromine, m and n are 0–3 with the proviso that terminal carbon atoms are independently perhalogenated or fully hydrogenated, the solvents boil at $-15°$ C. to 40° C. at atmospheric pressure, and the solvent to dichlorobutene ratio is from 2.0:1 to 11:1. The heat of reaction is removed by vaporization of solvent and 1,3-butadiene and returning the ingredients to the reactor.

11 Claims, 1 Drawing Sheet

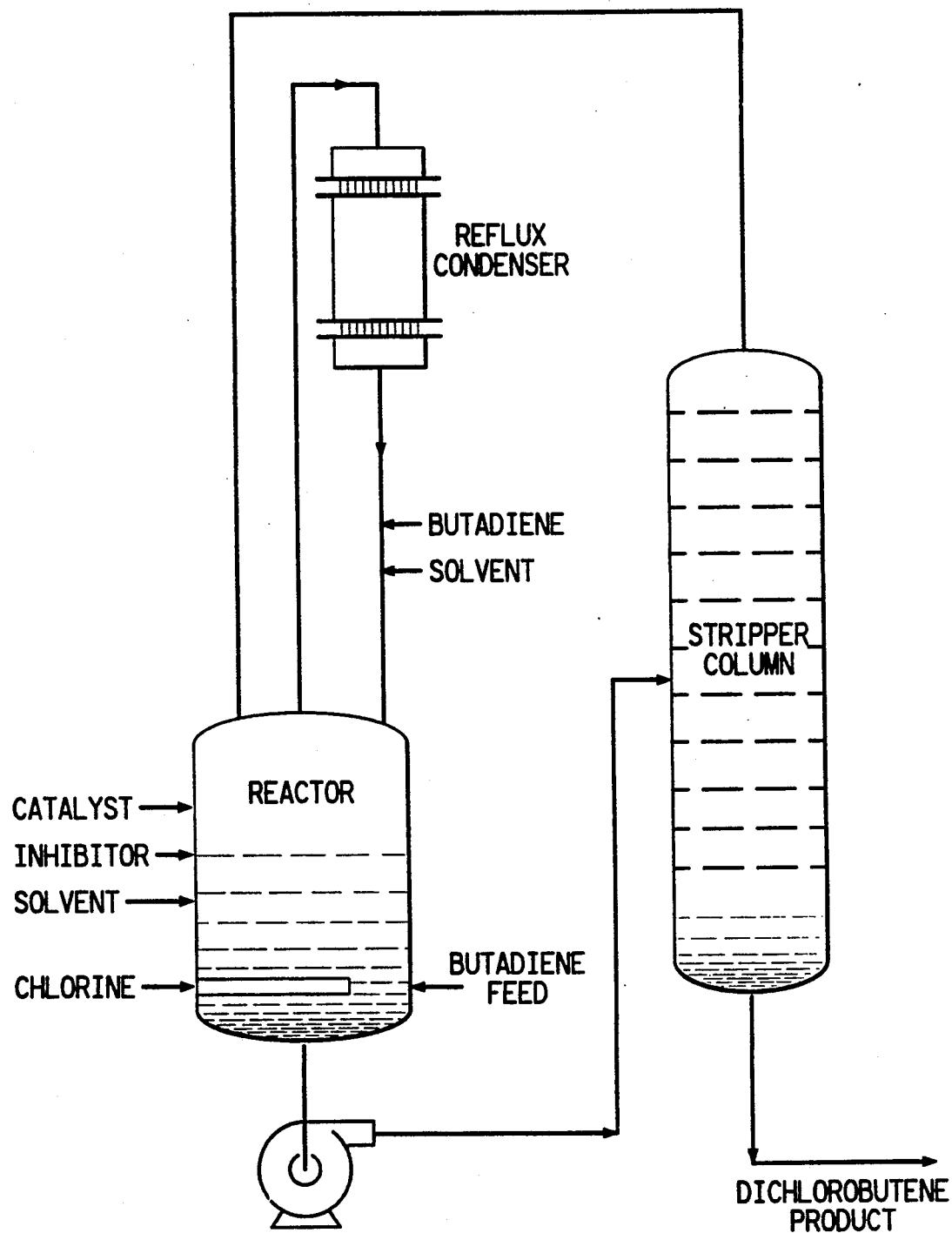

PROCESS FOR THE LIQUID PHASE CHLORINATION OF 1,3-BUTADIENE

RELATED APPLICATIONS

This application is a continuation-in-part of U.S. patent application Ser. No. 07/438,549, filed Nov. 17, 1989 now abandoned.

BACKGROUND OF THE INVENTION

This invention relates to an improved process for the liquid phase chlorination of 1,3-butadiene to 3,4-dichlorobutene-1 and 1,4-dichlorobutene-2, which is characterized by high yield, low solvent:product ratio, good specificity, low operating temperature, and results in ready and economical removal of unreacted 1,3-butadiene and solvent for reuse in the system.

1,4-dichlorobutene-2 is a valuable intermediate in the manufacture of certain important polyamides, such as Nylon 66, while 3,4-dichlorobutene-1 is an equally valuable intermediate in the manufacture of chloroprene, which is the basic monomer in the manufacture of a class of important synthetic rubbers known as the neoprenes.

3,4-dichlorobutene-1 and 1,4-dichlorobutene-2 are prepared commercially from 1,3-butadiene in vapor phase chlorination processes utilizing either adiabatic reactors or tubular reactors. In both methods the free radical chlorination process requires the use of large excesses of butadiene which are recycled and in addition the processes are characterized by low yields (about 91.1%), nonspecificity, and high temperatures of the order of 225°-300° C.

It is also known to chlorinate 1,3-butadiene in the presence of halogenated solvents in the liquid phase, for example in systems catalyzed by soluble quaternary ammonium, pyridinium, phosphonium, and sulfonium chlorides, as described in British Patent No. 1,435,826, or in the presence of ferric chloride catalysts, as described in German Patent No. 2347194 to produce 3,4-dichlorobutene-1 and 1,4-dichlorobutene-2 and in a plug-flow reactor as described in U.S. Pat. No. 2,369,117. Despite the fact that liquid phase chlorination results in higher yields of the desired 3,4-dichlorobutene-1 and 1,4-dichlorobutene-2 products compared to vapor phase processes, liquid phase chlorination has not been commercially attractive. This is primarily due to the operating costs for energy and large investment required for equipment to separate solvent from the low boilers, dichlorobutene products, and high boilers in several distillation columns and the additional investment in equipment to handle the larger process streams.

An object of this invention is to provide a liquid phase chlorination process that allows a reduction in solvent:dichlorobutene ratio compared to prior art processes and simplifies recovery of the valuable dichlorobutene products and unreacted 1,3-butadiene, especially a process that precludes the necessity for secondary distillation facilities to remove large amounts of solvent from the dichlorobutenes and low and high boiling by-products. Also, because the process of this invention provides for low reaction temperatures the amount of by-products formed during the chlorination of 1,3-butadiene is reduced with a concomitant increase in the yield of the desired dichlorobutenes, significantly above 91%, yields usually obtained in vapor phase processes.

SUMMARY OF THE INVENTION

The present process provides for a low temperature liquid phase chlorination reaction of 1,3-butadiene to dichlorobutene in an evaporatively cooled reactor in which relatively small quantities of solvent are employed because evaporation and reflexing of solvent and 1,3-butadiene to the reactor provide means for controlling the reaction temperature. The relatively small amount of solvent associated with the product stream is readily removed from the chlorinated products. More specifically, the invention is directed to a continuous process for the liquid phase chlorination of 1,3-butadiene to produce a mixture of 3,4-dichlorobutene-1 and 1,4-dichlorobutene-2 which comprises contacting in an evaporatively cooled reactor 1,3-butadiene with elemental chlorine in a solvent in the presence of a chlorination catalyst at a temperature of about 25°-100° C. and at a pressure sufficient to give the resulting reaction mixture a boiling point of from about 25°-100° C., said solvent being the hydrocarbons butane or pentane or a fluorinated solvent represented by the formula:

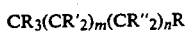

where R is independently hydrogen, fluorine, chlorine or bromine, R' is hydrogen, R" is independently fluorine, chlorine or bromine, m and n are 0-3, with the proviso that terminal carbon atoms are independently perhalogenated or fully hydrogenated, said solvents having boiling points of from about $-15°$ C. to 40° C. at atmospheric pressure, the solvent to dichlorobutene ratio is from 2.0:1 to 11:1, preferably 3:1 to 6:1, and said solvent being substantially inert to reaction with elemental chlorine at reaction conditions, removing the heat of reaction by vaporizing solvent and unreacted 1,3-butadiene in an overhead stream, and condensing said solvent and butadiene and returning said solvent and butadiene to the reactor, while, at the same time, bottoms from the reactor containing the dichlorobutenes, a portion of the unreacted 1,3-butadiene and solvent, are fed to a stripper column where the 1,3-butadiene and solvent are separated from the dichlorobutenes and by-products and recycled in a single stream to the reactor and the dichlorobutenes from the bottom of the stripper column are recovered.

DETAILED DESCRIPTION OF THE INVENTION

The process of the present invention involves feeding elemental chlorine and 1,3-butadiene to an evaporatively cooled reactor containing a selected solvent. Minor amounts of a free radical inhibitor are added to reduce or eliminate free radical reactions and the formation of excessive amounts of hydrogen chloride. A catalyst, or catalyst precursor which forms the chlorination catalyst in situ, is added to increase the rate of formation of the dichlorobutenes and yields thereof. The reactor is operated at temperatures of from about 25°-100° C. The 1,3-butadiene and elemental chlorine react in the liquid phase to form dichlorobutene. The heat of reaction is removed by vaporization of some of the solvent and unreacted 1,3-butadiene. The vapors of the unreacted 1,3-butadiene and solvent that evaporate are condensed in a reflux condenser and returned in a single stream directly to the reactor. The bottoms from the reactor which is the product stream containing the dichlorobutenes, unreacted 1,3-butadiene, by-products and solvent, are fed to a stripper column or flasher where the crude dichlorobutene is separated by stripping the low boiling solvent and 1,3-butadiene in the overhead. The crude dichlorobutene containing minor amounts of low and high boiling by-products is fed to refining columns for purification. The overhead vapor of solvent and unreacted 1,3-butadiene from the stripping column is condensed and returned to the reactor as a single stream for reuse.

BRIEF DESCRIPTION OF THE DRAWING

Reference is now made to the flow sheet which describes the liquid phase chlorination process. Liquid 1,3-butadiene and gaseous elemental chlorine are fed to an evaporatively cooled reactor containing a solvent substantially inert to reaction with elemental chlorine. A free radical inhibitor can be added to the reactor to reduce or eliminate free radical chlorination of butadiene. A chlorination catalyst is added to increase the rate of the reaction, the yield of dichlorobutenes, and the isomer selectivity. The 1,3-butadiene and elemental chlorine react in the evaporatively cooled reactor in the liquid phase to form the dichlorobutenes. The heat of reaction is removed by vaporization of the solvent and unreacted 1,3-butadiene. The vapors of solvent and butadiene are removed overhead, from the reactor, condensed in a reflux condenser and returned to the evaporatively cooled reactor. The bottoms of the reactor containing the dichlorobutenes and a portion of the low boiling solvent and 1,3-butadiene are fed to a stripper column where the dichlorobutenes are recovered and the low boiling components primarily solvent and 1,3-butadiene, are removed in the overhead vapor from the stripper column and condensed and returned to the reactor.

The reaction of elemental chlorine, e.g., gaseous chlorine, with 1,3-butadiene is highly exothermic. The solvent used in the process acts as a diluent to improve yield and to evaporatively cool the reactor. As long as there is an excess of solvent and/or 1,3-butadiene, the reactor contents will boil and remove the heat of reaction.

Oxygen is present in small amounts as an impurity which is introduced when the solvent and chlorine are fed to the reactor. Generally, quantities of up to about 0.5% oxygen are present in the vapor space above the reaction mixture. Higher amounts of oxygen can be present in the vapor space above the mixture without any detrimental effect on the reaction. However, the presence of too great a quantity of oxygen result in a safety hazard in the system.

An important condition for obtaining the results sought requires the use of particular solvents in the process. The solvents used in the process are the hydrocarbons butane or pentane or a fluorinated solvent represented by the formula:

$$CR_3(CR'_2)_m(CR''_2)_nR$$

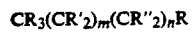

where R is independently hydrogen, fluorine, chlorine or bromine, R' is hydrogen, R" is independently fluorine, chlorine or bromine, and m and n are 0-3, with the proviso that the terminal carbon atoms are independently perhalogenated or fully hydrogenated. Further, the solvents have boiling points of $-15°$ C. to $40°$ C. at atmospheric pressure, the solvent to dichlorobutene product ratio is from 2.0:1 to 11:1, preferably 3:1 to 6:1, and said solvents are substantially inert to reaction with elemental chlorine at reaction conditions.

The solvents used in the chlorination process have boiling points relatively close to the boiling point of 1,3-butadiene ($-4°$ C.). i.e., $40°$ C. to $-15°$ C. The selection of such solvent allows both the solvent and unreacted 1,3-butadiene to be separated from the dichlorobutene in the product stream by a stripping column in one step. Recycle of the condensed mixture in a single stream is thus possible without additional equipment or energy. Furthermore, the use of solvents having boiling points close to that of 1,3-butadiene prevents 1,3-butadiene enrichment of the vaporized mixture of 1,3-butadiene and solvent in the vapor space above the reaction mixture which would otherwise occur if higher boiling solvents were used. Thus, 1,3-butadiene is more effectively utilized than in liquid phase chlorinations in which higher-boiling solvents are present. In addition, a low reaction temperature minimizes by-product formation. The fluorinated solvent can be represented by the formula:

$$CR_3(CR'_2)_m(CR''_2)_nR$$

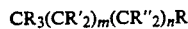

with the values for R, R', R" and m and n as given above. Preferably in the above formula R and R" are fluorine, chlorine or bromine and m equals 0. Perfluorinated solvents wherein R and R" are fluorine and m equals 0 are especially effective. If the boiling point of the solvent is above $40°$ C., the solvent will be difficult to separate from the low boiling by-products and the product dichlorobutenes without high investments in distillation equipment. On the other hand, if the boiling point of the solvent is too low, i.e., below $-15°$ C., it becomes difficult to condense, and low temperature refrigeration or high pressure compression are required to avoid excessive vent losses. Solvents that are used in the process of this invention are the hydrocarbons butane and pentane and representative fluorinated solvents include dichlorodifluoromethane, 1,1-dichlorotetrafluoroethane, 1,2-dichlorotetrafluoroethane, 1-chloro-1,1-fluoroethane, 1-chloroheptafluoropropane, 1,1,1,2,2-pentafluoropropane, perfluorobutane, 2,3-dichlorooctafluorobutane, and 2,2,3,3-tetrafluorobutane. Preferred solvents include butane, pentane, 1,1-dichloro-1-fluoroethane, and 1,2-dichlorotetrafluoroethane; the latter is especially preferred because its boiling point is very close to that of the butadiene and it is available in commercial quantities. The weight ratio of solvent to crude dichlorobutene in the reactor is from 2.0:1 to 11:1, preferably 3:1 to 6:1. Lower ratios lead to decreases in yield at the shorter residence times. Higher ratios are not economically attractive due to the larger amount of energy required to recover the solvent which must be separated with 1,3-butadiene from the products and by-products and the investment in equipment to handle the larger process streams containing solvent.

The chlorination process is conducted at a temperature of $25°-100°$ C., preferably $40°-60°$ C., and at a pressure sufficient to give the solution in the reactor, which consists of 1,3-butadiene, dichlorobutenes, and solvent, i.e., reaction mixture, a boiling point of from $25°-100°$ C., preferably $40°-60°$ C. The pressures under which the reaction is conducted will vary with the boiling point of the particular solvent used. In any event, the pressure employed is that sufficient to give the reaction mixture of 1,3-butadiene, the dichlorobutenes, and solvent a boiling point of from about 25°–100° C.

An important feature of the invention is the use of an evaporatively cooled isothermal reactor. The use of such a reactor is a principal element which allows the low solvent:product ratios which are a feature of the present invention. In plug flow and other reactors used in prior art liquid phase chlorination processes, temperature increases in the reaction mixture are kept within reasonable limits by allowing the very large quantities of solvent to act as heat sinks. Heat is removed by conventional heat exchange processes and other cooling means. In evaporatively cooled reactors, however, heat is removed by boiling and vaporization of liquid, a process which involves a phase change. The latent heat of vaporization provides the rapid mechanism for removal of the heat produced by the exothermic chlorination reactions rather than large volumes of solvent. Thus, the process of the present invention provides a high yield liquid phase chlorination process which does not require large amounts of organic solvents and which is economical on a commercial scale. In the process of the present invention the heat of the reaction is removed by boiling and vaporization of solvent and 1,3-butadiene which are condensed and returned to the reactor. In addition, isothermal conditions provide a safer process than prior art processes because uncontrollable runaway reactions are unlikely. Residence times in the reactor in the continuous process generally range from about 1.5 to 10 minutes. Residence times less than 1.5 minutes lead to a decrease in yield of dichlorobutenes and residence times in excess of 10 minutes are not economically attractive on a commercial scale due to the larger equipment required.

A catalyst is added to the reaction mixture to promote the ionic chlorination reaction. Such catalysts are well known in this technology. Suitable catalysts are chloride ion sources which may be added to the reaction mixture in the form of chloride salts or in the form of materials which will react with a component of the reaction mixture to produce a chloride salt in situ, i.e., catalyst precursor. Representative examples of suitable compounds which act as catalysts for the reaction are quaternary ammonium chlorides, quaternary phosphonium chlorides, and ternary sulfonium chlorides. Hydrochlorides of primary, secondary, or tertiary amines can also be used. Examples of materials which may be added to form the catalyst in situ include amines, either primary, secondary, or tertiary, or the analogous phosphides or sulfides. These compounds are capable of reacting with one or more of the chlorine-substituted materials in the reaction mixture or with hydrogen chloride to form a chloride ion source. Other examples of precursors for chloride ions are salts in which the anion is not a chloride ion but which can undergo an ion exchange reaction in the reaction medium to produce a chloride ion. Quaternary ammonium chlorides are a preferred catalyst type because they are widely available commercially as surface active agents. Representative quaternary ammonium compounds include butyltriethylammonium chloride, dilauryldimethylammonium chloride, amyltriethylammonium chloride, tetraoctylammonium chloride, hexyltrimethylammonium chloride, and the like. Suitable quaternary phosphonium compounds include, for example, tetrabutylphosphonium chloride, methyltrioctylphosphonium chloride, trimethyloctadecenylphosphonium chloride, and triethyl(2-bromoethyl)phosphonium chloride. Sulfonium compounds which may be used as catalysts include trimethylsulfonium chloride, dihexylethylsulfonium chloride, dihexylethylsulfonium chloride, methyldioctadecylsulfonium chloride, dibutylpropylsulfonium chloride, and cyclohexyldimethylsulfonium chloride. It is usually more convenient to form the catalyst in situ, for example by adding an amine as a free base which can then react to form the chloride ion source in the reaction mixture. Pyridine is particularly useful as a catalyst precursor. Other compounds which will form catalysts in situ in the reaction medium are the carboxylic acid amides such as formamide, acetamide, 2-pyrrolidone, 2-piperidone, and N-butylacetamide. The catalyst precursor concentration generally ranges from 20–200 ppm based on the amount of solvent present. Below 20 ppm there is a decrease in yield, and concentrations above 200 ppm are not cost effective.

The process is preferably, although not necessarily, carried out in the presence of free radical inhibitors. Conventional free radical inhibitors include phenols such as 4-tert-butyl catechol, aromatic amines, such as phenyl alphanaphthylamine, phenothiazine, and N-nitrosodiphenylamine, and other inhibitors, such as sulfur. Practical inhibitor concentrations have been found to be about 20–80 ppm based on the amount of solvent present. Concentrations below 20 ppm lead to decreases in yield, while concentrations over 80 ppm are not economical.

The reaction mixture or effluent coming from the chlorination reactor is fed to a refining column for separating the unreacted 1,3-butadiene and solvent from 3,4-dichlorobutene-1 and 1,4-dichlorobutene-2. The physical separation of the reaction stream into the two principal streams, i.e., 1,3-butadiene/solvent and the dichlorobutenes, can be accomplished by suitable means well known in the art. The physical separation of the reaction mixture can be performed, for example, in a stripper in which the reaction mixture is fed into the stripper column. Heat supplied to the bottom of the column causes vaporization of the reaction components. The lower boiling components consisting of 1,3-butadiene and solvent go overhead for recycling, as a single stream, to the reactor. The higher boiling components containing the dichlorobutenes and by-products are removed from the bottom of a column for further purification. Also conventional single stage flashers can be used to separate the reaction mixture for recirculation of the 1,3-butadiene/solvent to the reactor and recovery of the dichlorobutenes. Conventional distillation columns can also be used. Separation of the streams using a stripper column is preferred.

The following examples illustrate the invention wherein parts and percentages are by weight unless otherwise indicated.

EXAMPLE 1

A cylindrical evaporatively cooled nickel pressure reactor equipped with an agitation means and having interior dimensions of 23 cm in height by 7.8 cm in diameter was continuously fed with a stream of gaseous chlorine and a second stream consisting of 1,3-butadiene in the solvent 1,2-dichlorotetrafluoroethane. The fluorinated solvent has a boiling point of 4° C. at atmospheric pressure. The chlorine was introduced at the rate of 0.17 g/s. The rate of addition of the butadiene/solvent stream was 3.2 g/s (0.21 g butadiene/s and 3 g 1,2-dichlorotetrafluoroethane/s). The butadiene had a purity of 99.3%. The reactor was operated at a 15 cm liquid level which gave a residence time of 3.2 minutes at the feed rates used. An inhibitor, phenyl alpha-naphthylamine, dissolved in pyridine (chlorination catalyst precursor), was added to the reactor to give concentrations of 50 and 100 ppm respectively based on the solvent 1,2-dichlorotetrafluoroethane. The ratio of solvent to dichlorobutenes was 10. The reactor was operated at 323 K (50° C.) and a pressure of 445 kPa. Isothermal temperature at the boiling point was maintained by controlling the pressure in the reactor. Heat removal was provided by vaporization of solvent and unreacted butadiene which was removed overhead condensed and returned to the reactor. The reaction mixture, containing 3,4-dichlorobutene-1 and trans-1,4-dichlorobutene-2, unreacted 1,3-butadiene and solvent was removed from the bottom of the reactor and fed to a stripper column. Unreacted 1,3-butadiene and solvent were vaporized and removed overhead in the stripper column, subsequently condensed, and recycled to the reactor for reuse in the system. The dichlorobutenes were removed from the bottom of the column. The yield of dichlorobutenes was 96.3%, as determined by gas chromatography using a J&W fused silica capillary (Alltech 9385) DB-5 "Durabond" 60M×0.25 mm I.D. column with one coat of bonded 95% dimethyl, 5% diphenyl silicone operated at a maximum temperature of 250° C. The product had the following composition by weight:

| 3,4-dichlorobutene-1 | 46% |
| cis-1,4-dichlorobutene-2 | 1% |
| trans-1,4-dichlorobutene-2 | 47% |
| trichlorobutenes | 0.9% |
| tetrachlorobutanes | 4.2% |
| monochlorobutadienes | 0.6% |
| other | 0.5% |

EXAMPLE 2

The procedure described in Example 1 was repeated except n-pentane was used as the solvent. Gaseous chlorine and a second stream consisting of 1,3-butadiene in the solvent n-pentane of 99.3% purity were fed to the reactor. The solvent has a boiling point of 36° C. The chlorine was introduced at the rate of 0.22 g/s. The rate of addition of the butadiene/solvent stream was 1.83 g/s (0.34 butadiene/second and 1.5 g n-pentane/s). The butadiene had a purity of 99.4%. The reactor was operated at a 14 cm liquid level which gave a residence time of 4 minutes at the feed rates used. An inhibitor, phenyl alpha-naphthylamine, dissolved in pyridine (chlorination catalyst precursor), was added to the reactor to give concentrations of 60 and 100 ppm respectively based on the pentane solvent. The ratio of solvent to dichlorobutenes was 4. The reactor was operated at 330 K (57° C.) and a pressure of 310 kPa. Temperature control was provided by vaporization of solvent and unreacted butadiene which were removed overhead. These ingredients were condensed and returned to the reactor. The reaction mixture containing the dichlorobutenes, unreacted 1,3-butadiene and solvent was removed from the bottom of the reactor and fed to a stripper column. Unreacted 1,3-butadiene and solvent were vaporized and removed overhead in the stripper column, subsequently condensed, and recycled to the reactor for reuse in the system. The dichlorobutenes were removed from the bottom of the column. The yield of dichlorobutenes was 98.1% as determined by gas chromatography using a J&W fused silica capillary (Alltech 9385) DB-5 "Durabond" 60M×0.25 mm I.D. column with one coat of bonded 95% dimethyl, 5% diphenyl silicone operated at a maximum temperature of 250° C. The product had the following composition by weight:

| monochlorobutadienes | 0.58% |
| 3,4-dichlorobutene-1 | 48.5% |
| cis-1,4-dichlorobutene-2 | 1.3% |
| trans-1,4-dichlorobutene-2 | 46.5% |
| trichlorobutenes | 0.7% |
| tetrachlorobutanes | 1.8% |
| other | 0.3% |

EXAMPLE 3

An evaporatively cooled glass reactor having a diameter of 5 cm and a length of 15 cm was equipped with a magnetic mixer and a 0.1 sq. meter reflux condenser. Gaseous chlorine, liquid 1,3-butadiene, and the solvent n-butane, having a purity of 99.7%, was fed to the reactor. The solvent has a boiling point of −4° C. The chlorine was introduced at the rate of 0.1 g/s. The rate of addition of the butadiene was 0.12 g/s. The rate of addition of the solvent containing the catalyst precursor (pyridine) and inhibitor (phenyl alpha-naphthylamine) was 0.46 g/s. The butadiene had a purity of 99.3%. The reactor was operated at a 7.6 cm liquid level which gave a residence time of 2.5 minutes at the feed rates used. The inhibitor, phenyl alpha-naphthylamine, dissolved in pyridine (chlorination catalyst precursor), was added to the solvent to give concentrations of 40 and 170 ppm respectively based on the solvent n-butane. The ratio of solvent to dichlorobutenes was 2.5. The reactor was operated at 320 K (48° C.) and a pressure of 448 kPa. Temperature control was provided by vaporization of solvent and the unreacted butadiene which were removed overhead. These ingredients were condensed and returned to the reactor. The reaction mixture containing 3,4-dichlorobutene-1 and trans-1,4-dichlorobutene-2, unreacted 1,3-butadiene and solvent was fed to a stripper column. Unreacted 1,3-butadiene and solvent were vaporized and removed overhead in the stripper column, subsequently condensed, and recycled to the reactor for reuse in the system. The dichlorobutenes were removed from the bottom of the column. The yield of dichlorobutenes was 98% as determined by gas chromatography using J&W fused silica capillary (Alltech 9385) DB-5 "Durabond" 60M×0.25 mm I.D. column with one coat of bonded 95% dimethyl, 5% diphenyl silicone operated at a maximum temperature of 250° C. The product had the following composition by weight:

| monochlorobutadienes | 1.8% |
| 3,4-dichlorobutene-1 | 54% |
| cis-1,4-dichlorobutene-2 | 0.7% |
| trans-1,4-dichlorobutene-2 | 43% |
| trichlorobutenes | Trace |
| tetrachlorobutanes | Trace |
| other | Trace |

EXAMPLE 4

The procedure described in Example 3 was repeated except that the stream of gaseous chlorine was introduced at a rate of 3.6 g/minute and 1,3-butadiene was fed to the reactor at a rate of 4.1 g/minute. The solvent used was 1,1-dichloro-1-fluoroethane having a boiling point of 32° C., and introduced at the rate of 64 g/minute. The reactor was operated at 7.6 cm liquid level which gave a residence time of 2.5 minutes at the feed rates used. An inhibitor, phenyl alpha-naphthylamine, dissolved in pyridine (catalyst precursor) was added to the reactor to give concentrations of 40 and 100 ppm respectively based on the solvent 1,1-dichloro-1-fluoroethane. The ratio of solvent to the dichlorobutenes was 10. The reactor was operated at 318 K (45° C.) and a pressure of 172 kPa. Temperature control was provided by vaporization of solvent and butadiene which were vaporized and removed overhead. These ingredients are condensed and returned to the reactor. The reaction mixture containing the dichlorobutenes, unreacted 1,3-butadiene and solvent was removed from the bottom of the reactor and fed to a stripper column. Unreacted 1,3-butadiene and solvent in this stream were vaporized and removed overhead in the stripper column, subsequently condensed, and recycled to the reactor for reuse in the system. The dichlorobutenes were removed from the bottom of the column. The yield of dichlorobutenes was 96.3% as determined by gas chromotography using a J&W fused silica capillary 60M×0.25 mm I.D. column operated at maximum temperature of 250° C. The product had the following composition by weight:

| | |
|---|---|
| 3,4-dichlorobutene-1 | 45.37% |
| cis-1,4-dichlorobutene-2 | 0.99% |
| trans-1,4-dichlorobutene-2 | 47.19% |
| trichlorobutenes | 0.75% |
| tetrachlorobutane | 3.73% |
| monochlorobutadiene | 1.2% |
| other | 0.76% |

EXAMPLES 5-15

The procedure described above in Example 1 was repeated except that the parameters given in Table 1 below were substituted for those used in Example 1.

resulting reaction mixture a boiling point of from about 25°–100° C., said solvent being the hydrocarbons butane or pentane or a fluorinated solvent represented by the formula:

$$CR_3(CR'_2)_m(CR''_2)_nR$$

where R is independently hydrogen, fluorine, chlorine or bromine, R' is hydrogen, R" is independently fluorine, chlorine or bromine, m and n are 0-3, with the proviso that terminal carbon atoms are independently perhalogenated or fully hydrogenated, further the solvents having boiling points of from about −15° C. to 40° C. at atmospheric pressure, the solvent to dichlorobutene ratio is from 2.0:1 to 11:1 and said solvent being substantially inert to reaction with elemental chlorine at reaction conditions, removing the heat of reaction by vaporizing solvent and unreacted 1,3-butadiene in an overhead stream, and condensing said solvent and 1,3-butadiene and returning said solvent and 1,3-butadiene to the reactor, while, at the same time, bottoms from the reactor containing the dichlorobutenes, a portion of the unreacted 1,3-butadiene and solvent, are fed to a stripper column where the 1,3-butadiene and solvent are separated from the dichlorobutenes and by-products and recycled in a single stream to the reactor and the dichlorobutenes from the bottom of the stripper column are recovered.

2. A process of claim 1 wherein R and R" are fluorine, chlorine or bromine and m equals 0.

3. A process of claim 2 wherein R and R" are fluorine.

4. A process of claim 1 wherein R" is fluorine.

5. A process of claim 1 wherein the solvent in n-butane.

6. A process of claim 1 wherein the solvent is pentane.

7. A process of claim 1 wherein the solvent is 1,2-dichlorotetrafluoroethane.

8. A process of claim 1 wherein the chlorination reaction is conducted in the presence of a free radical inhibitor.

TABLE I

| EXAMPLE | YIELD* (%) | BUTADIENE/Cl₂ FEED MOL RATIO | SOLVENT** PRODUCT RATIO | REACTION TEMP (°C.) | RESIDENCE TIME (MIN) | PYRIDINE (ppm) IN SOLVENT*** | INHIBITOR (ppm) IN SOLVENT**** |
|---|---|---|---|---|---|---|---|
| 5 | 97 | 1.5 | 10 | 47 | 1.5 | 60 | 30 |
| 6 | 93 | 1.1 | 7.8 | 40 | 3.1 | 96 | 48 |
| 7 | 95.6 | 1.85 | 8.2 | 40 | 3.5 | 99 | 49 |
| 8 | 96.2 | 1.6 | 6 | 40 | 3.3 | 103 | 52 |
| 9 | 96.3 | 1.7 | 10.7 | 40 | 3.2 | 100 | 50 |
| 10 | 95.6 | 1.85 | 8.2 | 30 | 3.4 | 99 | 49 |
| 11 | 96.3 | 1.78 | 10 | 60 | 3.3 | 97 | 48 |
| 12 | 96.3 | 1.67 | 10 | 52 | 2.1 | 103 | 51 |
| 13 | 95.8 | 1.74 | 10.6 | 52 | 10.3 | 95 | 47 |
| 14 | 95.2 | 1.84 | 9.9 | 40 | 2.1 | 20 | 48 |
| 15 | 95.2 | 1.89 | 10.1 | 40 | 2.1 | 50 | 49 |

*yield % of 3,4-dichlorobutene-1 and cis and trans 1,4-dichlorobutene-2 from 1,3-butadiene.
**weight of dichlorobutenes to solvent 1,2-dichlorotetrafluoroethane exiting reactor, by wt.
***catalyst precursor, by wt.
****phenyl alpha-naphthylamine, by wt.

I claim:

1. A continuous process for the liquid phase chlorination of 1,3-butadiene to produce a mixture of 3,4-dichlorobutene-1 and 1,4-dichlorobutene-2 which comprises contacting in an evaporatively cooled reactor 1,3-butadiene with elemental chlorine in a solvent in the presence of a chlorination catalyst at a temperature of about 25°–100° C. and at a pressure sufficient to give the 9. A process of claim 1 wherein the reaction temperature is 40°–60° C.

10. A process of claim 1 wherein elemental chlorine is gaseous chlorine.

11. A process of claim 1 wherein the solvent to dichlorobutene ratio is from 3:1 to 6:1.

* * * * *